(12) United States Patent
Ackley et al.

(10) Patent No.: US 8,381,896 B2
(45) Date of Patent: Feb. 26, 2013

(54) EJECTION SYSTEM

(75) Inventors: E. Michael Ackley, Mannington, NJ (US); Mark Ford, Deptford, NJ (US); Vincent M. DeLuccia, Jr., Riverside, NJ (US)

(73) Assignee: Ackley Machine Corporation, Moorestown, NJ (US)

( * ) Notice: Subject to any disclaimer, the term of this patent is extended or adjusted under 35 U.S.C. 154(b) by 383 days.

(21) Appl. No.: 12/662,373

(22) Filed: Apr. 13, 2010

(65) Prior Publication Data

US 2010/0258405 A1 Oct. 14, 2010

Related U.S. Application Data

(60) Provisional application No. 61/202,850, filed on Apr. 13, 2009, provisional application No. 61/282,084, filed on Dec. 14, 2009.

(51) Int. Cl.
*B07C 5/344* (2006.01)
*B65G 43/00* (2006.01)

(52) U.S. Cl. ........................ 198/340; 198/474.1; 209/576

(58) Field of Classification Search .................. 198/340, 198/474.1, 634; 209/576; 425/350; 356/237.1
See application file for complete search history.

(56) References Cited

U.S. PATENT DOCUMENTS

| | | | | |
|---|---|---|---|---|
| 3,960,292 A * | 6/1976 | Knapp | | 221/211 |
| 4,377,971 A * | 3/1983 | Ackley | | 101/40 |
| 5,085,510 A | 2/1992 | Mitchell | | |
| 5,538,125 A * | 7/1996 | Berta | | 198/345.3 |
| 5,695,043 A * | 12/1997 | Maezuru et al. | | 198/689.1 |
| 5,746,323 A * | 5/1998 | Dragotta | | 209/539 |
| 5,957,306 A * | 9/1999 | Hoffman | | 209/587 |
| 6,286,421 B1 * | 9/2001 | Ackley | | 101/38.1 |
| 7,102,741 B2 * | 9/2006 | Ackley et al. | | 356/237.1 |
| 7,217,381 B2 * | 5/2007 | Sowden | | 264/250 |
| 7,361,006 B2 * | 4/2008 | Sowden et al. | | 425/215 |
| 7,456,946 B2 * | 11/2008 | Ackley et al. | | 356/237.1 |
| 7,530,804 B2 * | 5/2009 | Sowden | | 425/112 |
| 7,701,568 B2 * | 4/2010 | Ackley et al. | | 356/237.1 |
| 7,797,909 B2 * | 9/2010 | Ream et al. | | 53/54 |
| 8,072,590 B2 * | 12/2011 | Ackley et al. | | 356/237.1 |

* cited by examiner

*Primary Examiner* — Douglas Hess

(74) *Attorney, Agent, or Firm* — Nixon & Vanderhye P.C.

(57) ABSTRACT

A conveyer apparatus for transporting and processing tablets includes a conveyer and an ejection system. Each of the tablets includes a first side, a second side opposite the first side, and a belly band that interconnects the first and second sides. The conveyer includes a plurality of carrier links to convey a plurality of tablets along a predetermined conveyer path. Each carrier link has a pocket to receive and transport a tablet in a vertical orientation along the predetermined conveyer path. The ejection system is structured to selectively accept or eject a tablet from the carrier link in response to a signal provided by a sensor positioned upstream of the ejection system. The ejection system includes at least one ejection finger movable between a non-ejection position in which the ejection finger is positioned out of the conveyer path of the carrier link and an ejection position in which the ejection finger is positioned with respect to the carrier link to contact and eject the tablet from the carrier link. At least a portion of the ejection finger defines a width that is smaller than a tablet width of the tablet and larger than a link width of the carrier link.

31 Claims, 11 Drawing Sheets

EJECTION SYSTEM

CROSS-REFERENCE TO APPLICATION

This application claims the benefit of U.S. Provisional Application Nos. 61/202,850, filed Apr. 13, 2009, and 61/282,084, filed Dec. 14, 2009, each of which is incorporated herein by reference in its entirety.

FIELD OF THE INVENTION

The present invention relates to an apparatus for conveying, inspecting, and ejecting pellet-shaped articles (e.g., tablets) in separate discharge chutes/outlets based on predetermined criteria.

BACKGROUND OF THE INVENTION

Processing of tablets, such as inspecting, marking, and/or laser drilling of tablets, is known in the art. Inspection units are typically configured to inspect and remove tablets from a conveyer mechanism that have been improperly processed in a previous processing operation. Previous processing operations may include marking the tablets with indicia, coloring the tablets, laser drilling holes in the tablets, and/or coating the tablets. These processing operations are typically completed upstream from the inspection unit such that the inspection unit may inspect if these processes have been properly completed.

It is important for the manufacturer to carefully inspect the pellet-shaped articles for defects, such as an improperly printed or coated side of the article, before the pellet-shaped article is distributed to the consumer so as to ensure the quality of the product and hence protect the safety of the consumer. Moreover, such defective articles must be separated from the acceptable articles based on the inspection results.

SUMMARY OF THE INVENTION

An aspect of the present invention relates to a product ejection (rejection) system designed to divert product (e.g., pharmaceutical tablets, capsules, confections, etc.) into two or more machine discharge chutes or outlets in response to a signal, e.g., a low voltage electrical signal. The ejection system is designed to be used on a single-lane tablet conveying system, e.g., such as an Ackley VIP® printer. The ejection system can be used in combination with an inspection or counting system to divert tablets to separate discharge points on the machine based on predetermined criteria such as inspection results or a specific tablet count.

Another aspect of the invention relates to a conveyer apparatus for transporting and processing tablets. The conveyer apparatus includes a conveyer and an ejection system. Each of the tablets includes a first side, a second side opposite the first side, and a belly band that interconnects the first and second sides. The conveyer includes a plurality of carrier links to convey a plurality of tablets along a predetermined conveyer path. Each carrier link has a pocket to receive and transport a tablet in a vertical orientation along the predetermined conveyer path. The ejection system is structured to selectively accept or eject a tablet from the carrier link in response to a signal provided by a sensor positioned upstream of the ejection system. The ejection system includes at least one ejection finger movable between a non-ejection position in which the ejection finger is positioned out of the conveyer path of the carrier link and an ejection position in which the ejection finger is positioned with respect to the carrier link to contact and eject the tablet from the carrier link. At least a portion of the ejection finger defines a width that is smaller than a tablet width of the tablet and larger than a link width of the carrier link.

Another aspect of the invention relates to a conveyer apparatus for transporting and processing tablets. The conveyer apparatus includes a conveyer and an ejection system. Each of the tablets includes a first side, a second side opposite the first side, and a belly band that interconnects the first and second sides. The conveyer includes a plurality of carrier links to convey a plurality of tablets along a predetermined conveyer path. Each carrier link has a pocket to receive and transport a tablet in a vertical orientation along the predetermined conveyer path. The ejection system is structured to selectively accept or eject a tablet from the carrier link in response to a signal provided by a sensor positioned upstream of the ejection system. The ejection system includes a pair of ejection fingers positioned on respective sides of the carrier links. The ejection fingers are movable between a non-ejection position in which the ejection fingers are positioned out of the conveyer path of the carrier link and an ejection position in which the ejection fingers are positioned with respect to the carrier link to contact and eject the tablet from the carrier link. The ejection fingers define a width therebetween that is smaller than a tablet width of the tablet and larger than a link width of the carrier link.

Another aspect of the invention relates to a conveyer apparatus for transporting and processing tablets. Each of the tablets includes a first side, a second side opposite the first side, and a belly band that interconnects the first and second sides. The conveyer apparatus includes a single row conveyer and an ejection system. The single row conveyer includes a plurality of carrier links to convey a plurality of tablets along a predetermined conveyer path. Each carrier link has a pocket to receive and transport an individual tablet in a vertical orientation along the predetermined conveyer path. The ejection system is structured to selectively accept or eject a tablet from the carrier link in response to a signal provided by a sensor positioned upstream of the ejection system. The sensor is configured to generate the signal based on one or more predetermined criteria, and the ejection system includes at least one ejection finger to eject only the selected tablet from the carrier link without affecting tablets in adjacent carrier links not associated with the predetermined criteria.

Another aspect of the invention relates to a method for transporting and processing tablets. The method includes conveying a plurality of tablets along a predetermined conveyer path within carrier links that transport individual tablets in a vertical orientation, sensing the tablets for one or more predetermined criteria, and ejecting only a selected tablet from the carrier link based on the predetermined criteria without affecting tablets in adjacent carrier links not associated with the predetermined criteria.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

Figure 1:
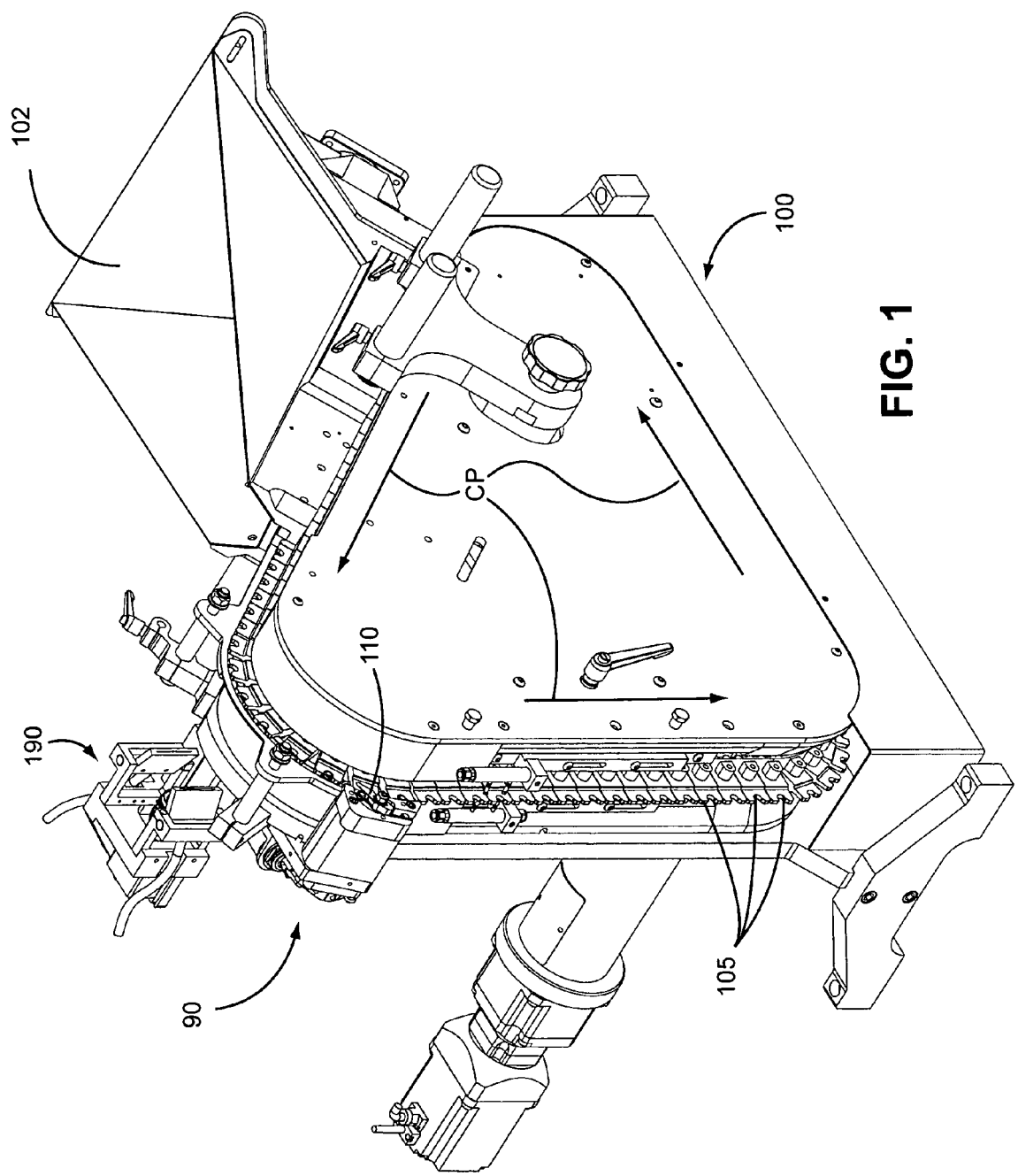
FIG. 1 is a perspective view of a conveyer apparatus including an ejection system according to an embodiment of the invention.

FIG. 1 illustrates a conveyer apparatus 100 including a plurality of product carrier links 105 structured to transport or convey a plurality of pellet-shaped articles along a predetermined conveyer path. In the illustrated embodiment, the pellet-shaped articles are in the form of tablets T as described below. However, it should be appreciated that the carrier links may be adapted for use with other pellet-shaped articles, e.g., capsules, pills, etc.

Figure 2:
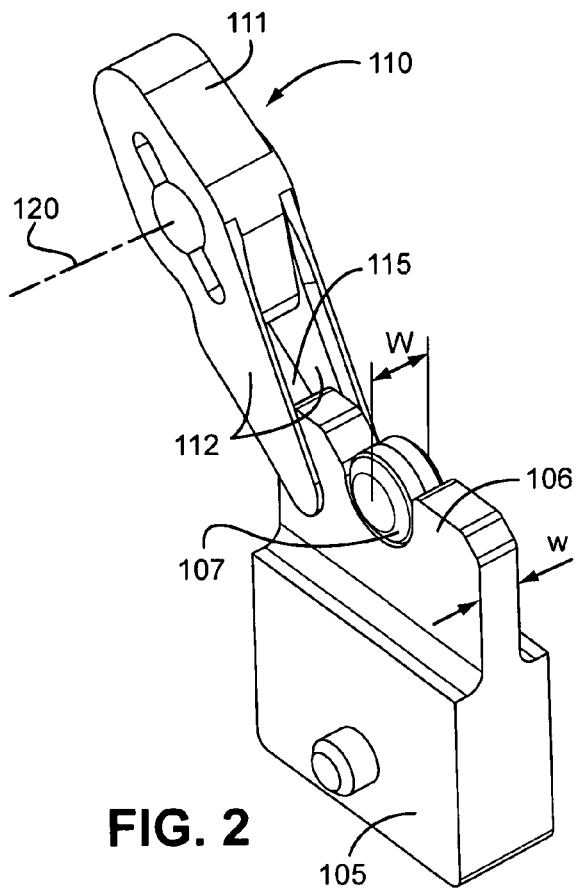
FIG. 2 is a perspective view of an ejection finger of the ejection system and a carrier link of the conveyer apparatus according to an embodiment of the invention.
Figure 3:
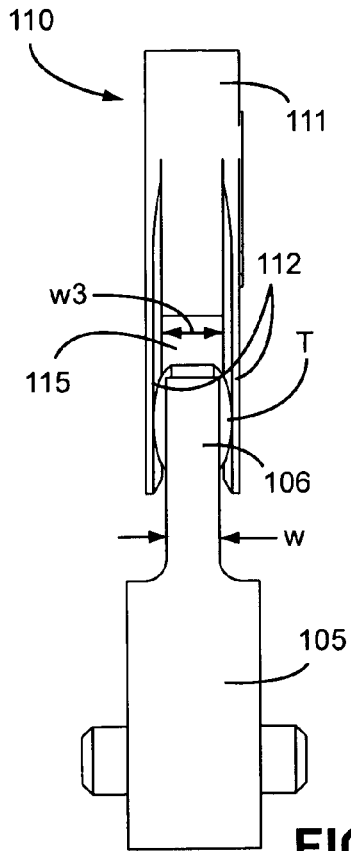
FIG. 3 is a front view of the ejection finger and carrier link of FIG. 2.

As best shown in FIGS. 2 and 3, each tablet T includes a first side 162, a second side 164 opposite the first side, and a belly band 166 that interconnects the first and second sides. The first and second sides may have a convex configuration, and the width of the belly band may vary.

The apparatus may be a ramp-type conveyer including incline, horizontal, and decline portions as disclosed in U.S. Pat. No. 5,655,453, which is incorporated by reference in its entirety. The conveyer path CP represents the direction of travel of the carrier links 105.

In the illustrated embodiment, each of the carrier links 105 includes a tablet carrier portion 106 that provides a single tablet receiving pocket 107. Each pocket includes a contoured bottom wall structured to receive and hold an individual tablet on-edge or around a portion of the belly band in a vertical or upright position. The tablet is carried within the carrier link in an upright position so that both sides of the tablet may be exposed to processing, e.g., inspection and/or marking, etc. However, it should be appreciated that each carrier link may be adapted to hold more than one tablet.

The pockets of the carrier links operate to receive and entrain tablets from a tablet dispenser 102, e.g., feed hopper or other product feeder as shown in FIG. 1, and move the tablets along the conveyer path. The tablet dispenser may be provided along an incline portion of the conveyer. In the illustrated embodiment, the dispenser may be configured to receive a supply of tablets and deliver individual tablets into respective pockets of carrier links. That is, the dispenser may be structured to feed individual tablets on-edge into a respective pocket of a carrier link. For example, the dispenser may include a funnel that tapers along the conveyer path so as to deliver individual tablets into a respective pocket. However, other feeding arrangements are possible.

The carrier links 105 are conveyed past an ejection system 90 according to an embodiment of the present invention. As described below, the ejection system 90 is structured to eject a tablet from the carrier link in response to a signal from an inspection unit or sensor, e.g., adapted to detect defective or flawed tablets. That is, the tablet is inspected by an inspection unit for one or more particular criteria or characteristics (e.g., printing misregistration, logo error, specific tablet count, etc.), and then brought past the ejection system 90 where unacceptable or flawed tablets as determined by the inspection unit are ejected into a discharge chute. In the illustrated embodiment, only tablets that have not met the particular characteristics will be ejected into the discharge chute. However, it should be appreciated that the opposite arrangement may be provided, e.g., acceptable tablets that have met the particular characteristics may be ejected into the discharge chute, such that all tablets (including defective tablets) are ejected in the event of solenoid failure.

It should be appreciated that the apparatus may be in the form of a printer with one or more processing stations (e.g., printing or marking apparatus, etc.) provided along the apparatus upstream of the ejection system. Alternatively, such processing stations may be provided in a separate apparatus, and then processed tablets may be delivered to the apparatus for inspection and possible ejection by the ejection system.

FIGS. 1-13 illustrate an ejection system 90 according to an embodiment of the invention. As illustrated, the ejection system 90 includes an ejection finger 110 that is pivotable about an axis 120 between an ejection position (e.g., solid lines in FIG. 5) and a non-ejection or normal position (e.g., phantom lines in FIG. 5). In the ejection position, the ejection finger is positioned with respect to a carrier link to contact and eject a tablet from the carrier link. In the non-ejection position, the ejection finger is positioned out of the path of the carrier link to allow the carrier link and tablet held therein to pass thereby without diverting or ejecting the tablet.

Figure 4:
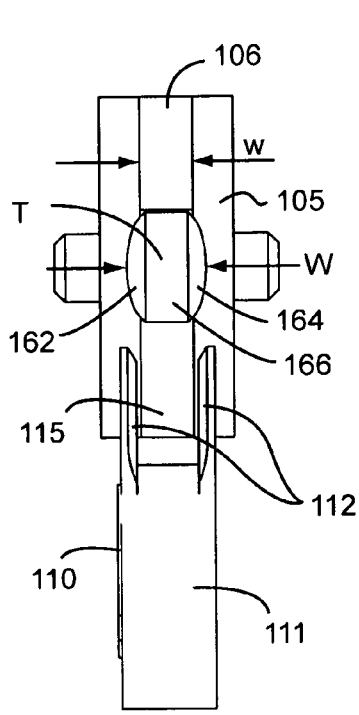
FIG. 4 is a top view of the ejection finger and carrier link of FIG. 2.

As best shown in FIGS. 2-4, the tablet carrier portion 106 of each link 105 has a link width (w) that is smaller than the tablet width W of the tablet T. Tablet T is carried within link 105 in an upright position, so this arrangement allows the tablet to protrude from one or both sides of the carrier link. In another embodiment, each carrier link may include a slot therethrough to expose the tablet for processing (e.g., an ejection finger may protrude through the slot to eject a tablet), in which case the tablet may have a width that is greater or less than, or equal to, the width of the tablet carrier portion of each link.

The ejection finger 110 has a main body 111 and spaced-apart tablet engaging members 112 extending from the main body. The tablet engaging members 112 define a slotted opening 115 whose width w3 (e.g., see FIG. 3) is larger than the width w of the tablet carrier portion 106 of each carrier link 105, but smaller than the tablet width W. This arrangement allows the tablet carrier portion 106 of each carrier link 105 to pass through the ejection finger's slotted opening 115, but not the tablet T.

The ejection finger 110 is moved from the non-ejection position to the ejection position in response to a signal from an inspection unit or sensor. In the illustrated embodiment, the sensor (e.g., camera unit 190 shown in FIG. 1) is provided upstream of the ejection system 90 and determines whether each tablet is acceptable or non-defective. The sensor sends a signal to the ejection system when the tablet is determined to be defective. In exemplary embodiments, a single camera may be provided to sense one side of the tablet, a pair of cameras may be provided to sense respective sides of the tablet, or a single camera along with an arrangement of mirrors may be provided to allow sensing of both sides of the tablet. When such signal is received by the ejection system to eject a tablet, e.g., when the sensor provides a signal indicative of a product flaw (such as printing misregistration), the ejection finger 110 pivots from the non-ejection position (see FIGS. 7 and 9) to the ejection position (see FIGS. 6 and 8) in the path of the carrier link.

Figure 5:
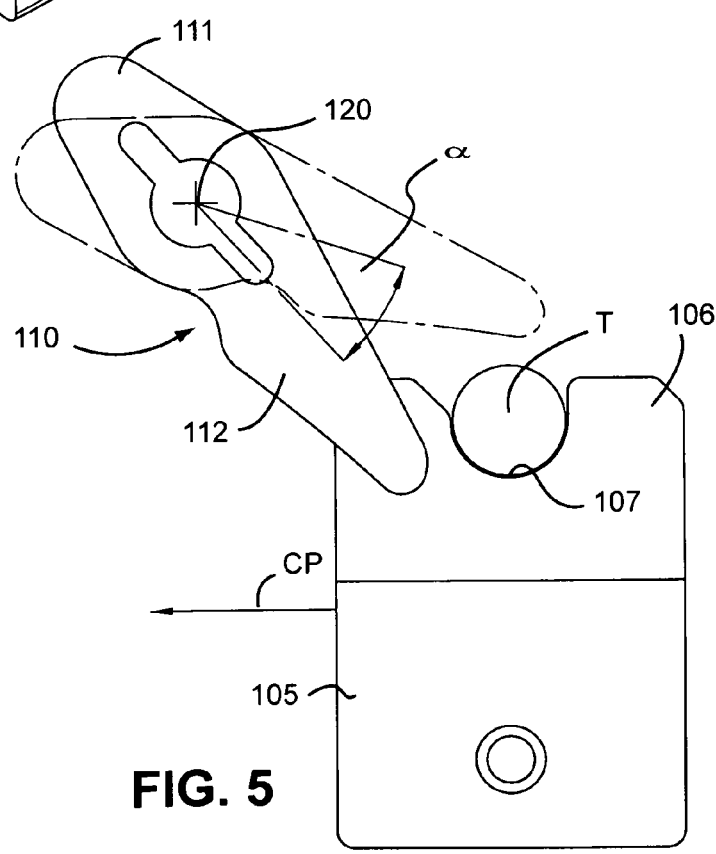
FIG. 5 is a side view of the ejection finger and carrier link of FIG. 2.
Figure 6:
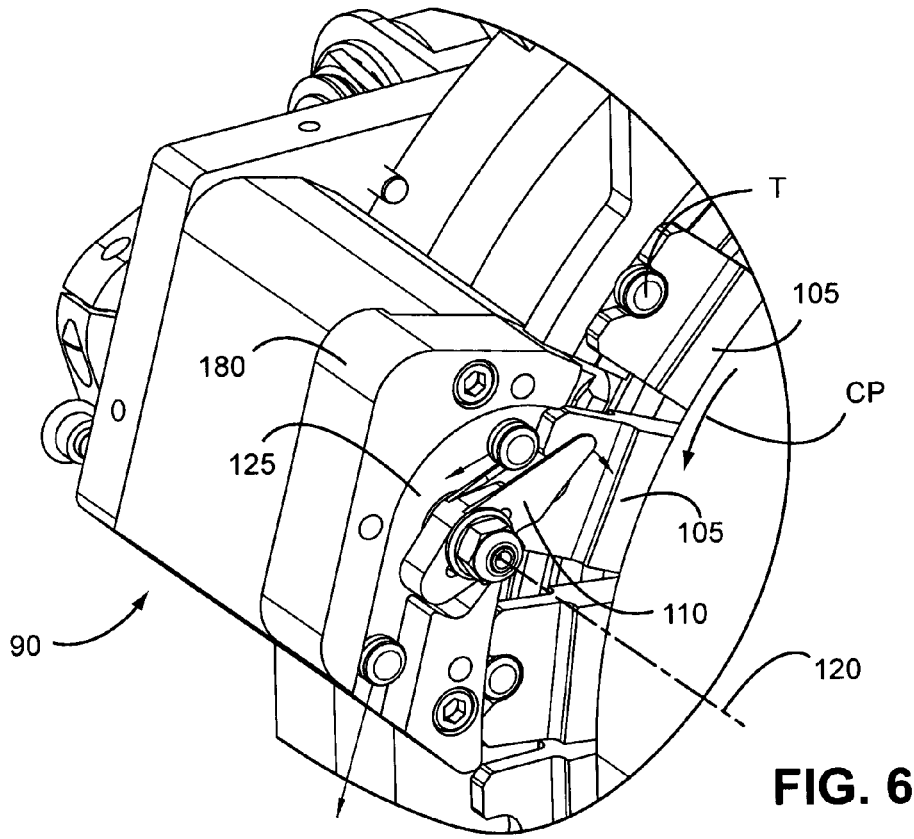
FIG. 6 is a perspective view of the ejection finger in an ejection position according to an embodiment of the invention.

When the ejection finger 110 is pivoted into the ejection position to eject a tablet (solid lines in FIG. 5), it is positioned at an angle a with respect to the direction of travel of the carrier link as shown in FIG. 5. This angle is the path that the tablet will travel when it is diverted by the ejection finger. The magnitude of the angle ranges from about 10-50°, e.g., about 30°.

Figure 8:
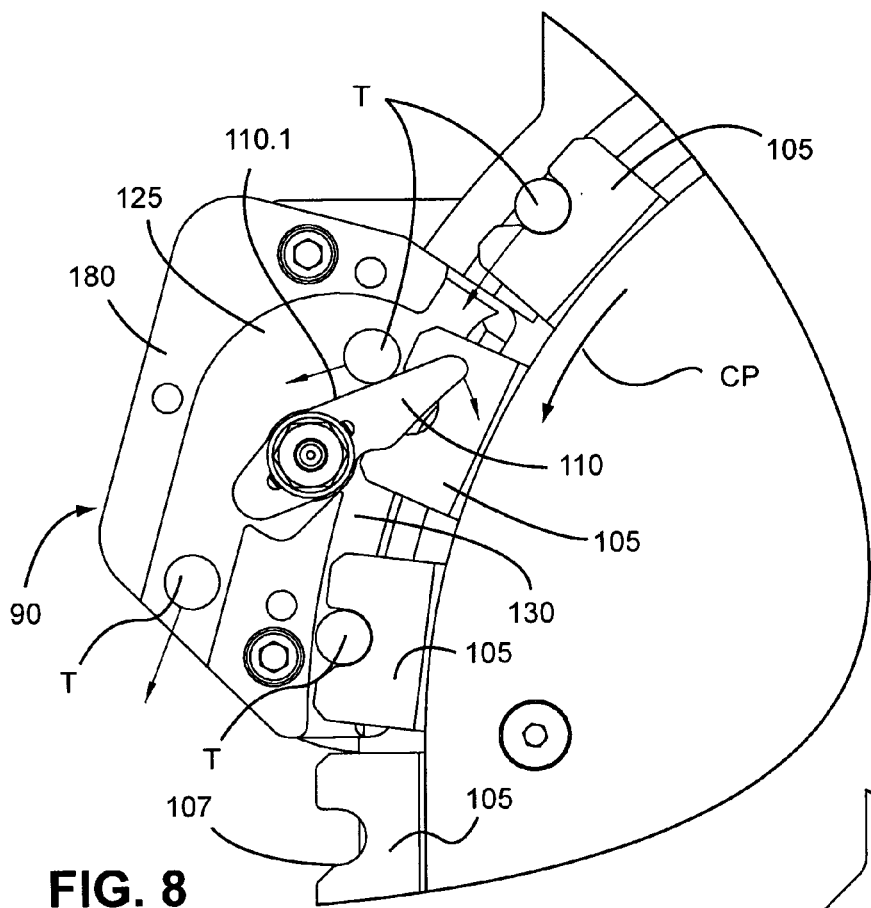
FIG. 8 is a side view of the ejection finger in an ejection position according to an embodiment of the invention.

As the carrier link 105 is conveyed past the ejection finger 110, the sides of the tablet T contact the tablet engaging members 112 of the ejection finger 110. As best shown in FIGS. 1 and 8, the ejection finger 110 is positioned on that part of the transport or conveyer path that transitions or has transitioned from horizontal to vertical. Thus, removal of the tablet T from the pocket 107 of the link 105 can be aided by gravity. When in the ejection position shown in FIGS. 6 and 8, the upper surface/edge 110.1 of finger 110 is oriented such that it is ramped or angled slightly downward from horizontal, e.g., about 15-25° or about 20°, or greater than about 5°. Tablet T may but does not necessarily roll on upper surface/edge 110.1.

The carrier link 105 continues to travel past the finger 110, while the tablet T is lifted out of the carrier link pocket 107 by the ejection finger 110. Thus, it is possible to selectively eject a single tablet T from its carrier link, without affecting the travel of adjacent (non-defective) tablets T, e.g., without also removing the non-defective tablets preceding or following the defective tablet.

The tablet is discharged along a channel 125 provided within a housing part 180 of the ejection system and through an opening at the bottom of the ejection system, and is diverted to a unique discharge chute for "defective" tablets on the apparatus.

Figure 7:
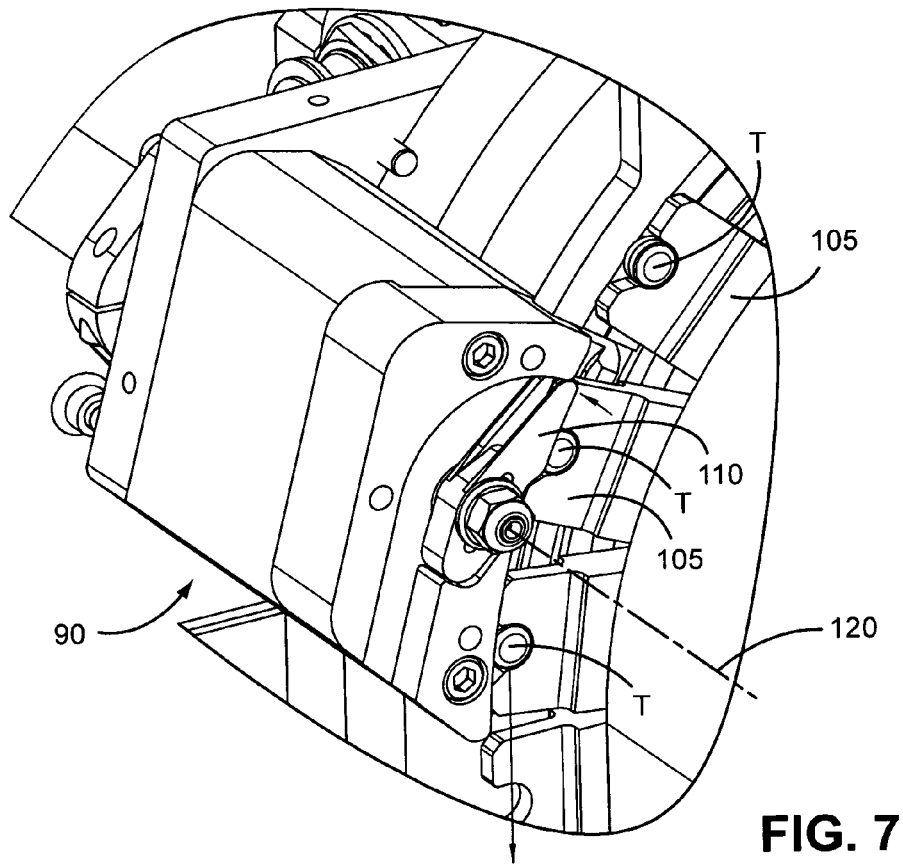
FIG. 7 is a perspective view of the ejection finger in a non-ejection position according to an embodiment of the invention.
Figure 9:
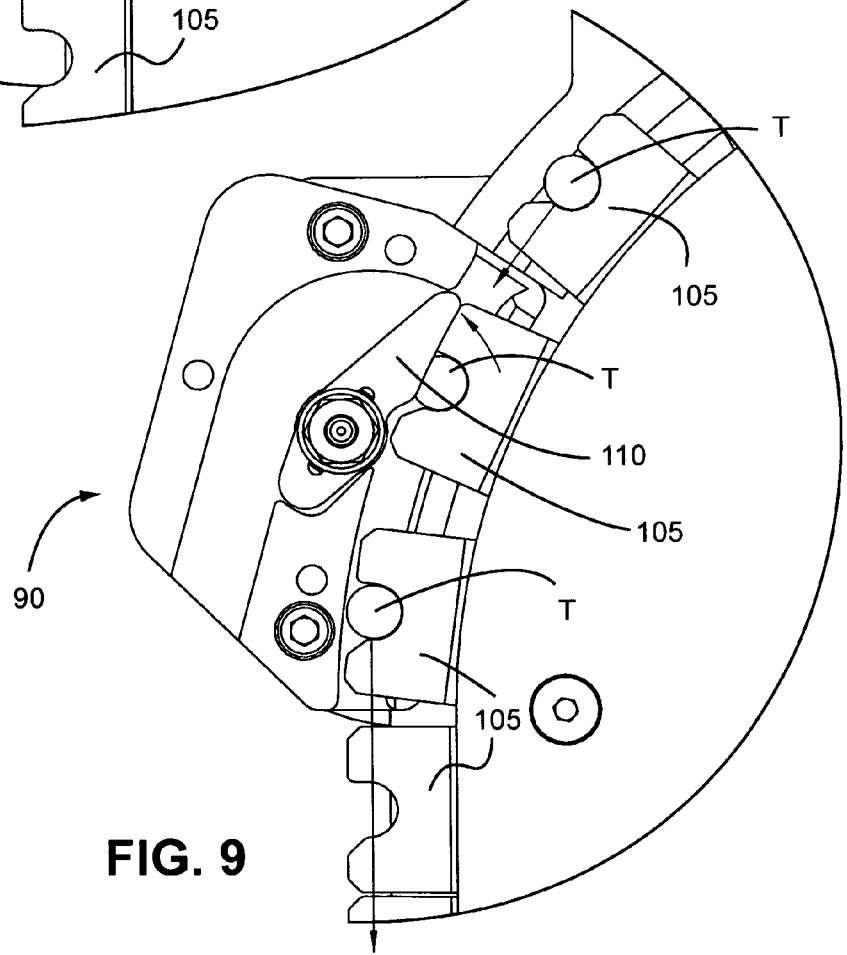
FIG. 9 is a side view of the ejection finger in a non-ejection position according to an embodiment of the invention.

After the carrier link has traveled past the ejection point provided by the ejection finger, the ejection finger is pivoted back into the non-ejection position and out of the path of the carrier links (e.g., see FIGS. 7 and 9).

The "acceptable" tablets T are allowed to pass through the ejection system along path 130, without being diverted by the ejection finger 110, and are discharged into a separate unique machine discharge chute for "acceptable" tablets. The path 130 is defined by a channel 135 within the housing part 180.

Pivotal movement of the ejection finger is effected by a low voltage linear electric solenoid, which is selectively actuated by the signal from the sensor. As shown in FIGS. 10-13, the ejection finger 110 is mounted to one end of a shaft 116. The opposite end of the shaft 116 is mounted to a linkage plate 150, which plate is coupled to a solenoid plunger 142 of the solenoid 140.

Figure 11:
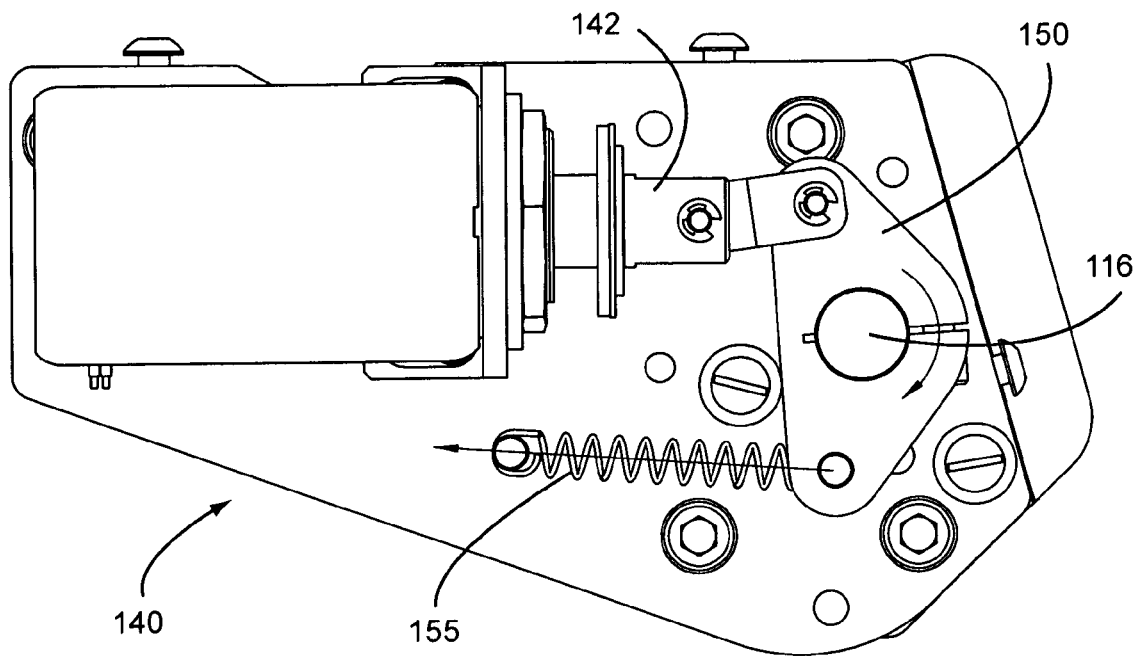
FIG. 11 is a side view of the ejection system in a non-ejection position according to an embodiment of the invention.
Figure 12:
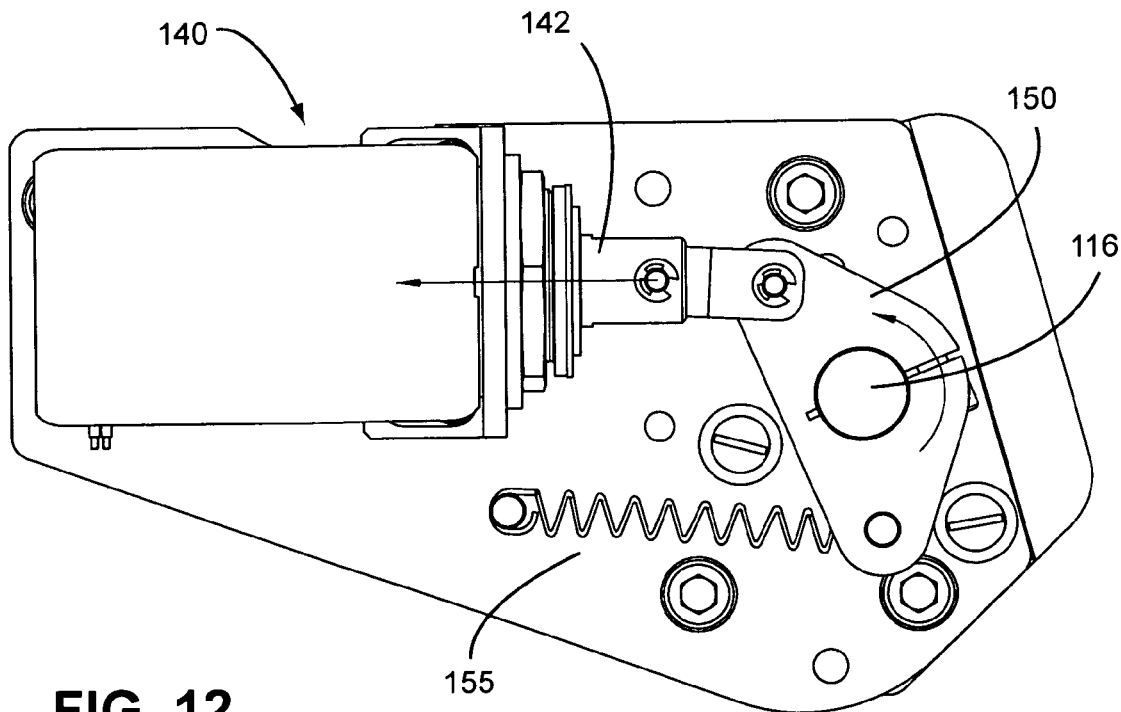
FIG. 12 is a side view of the ejection system in an ejection position according to an embodiment of the invention.

When a low voltage signal is sent to the solenoid 140 by the sensor, the plunger 142 is retracted into the solenoid body (i.e., the plunger 142 moves from the extended position shown in FIG. 11 to the retracted position shown in FIG. 12), which moves the linkage plate 150 to pivot the shaft 116 and hence pivot the ejection finger into the path of the carrier links.

When the low voltage signal is turned off, a spring 155 is used to pivot the ejection finger back to the normal position, out of the path of the carrier links. In an alternative, the spring can be used to bias the ejection finger into the path, and the solenoid can be activated to pivot the ejection finger out of the path.

Figure 10:
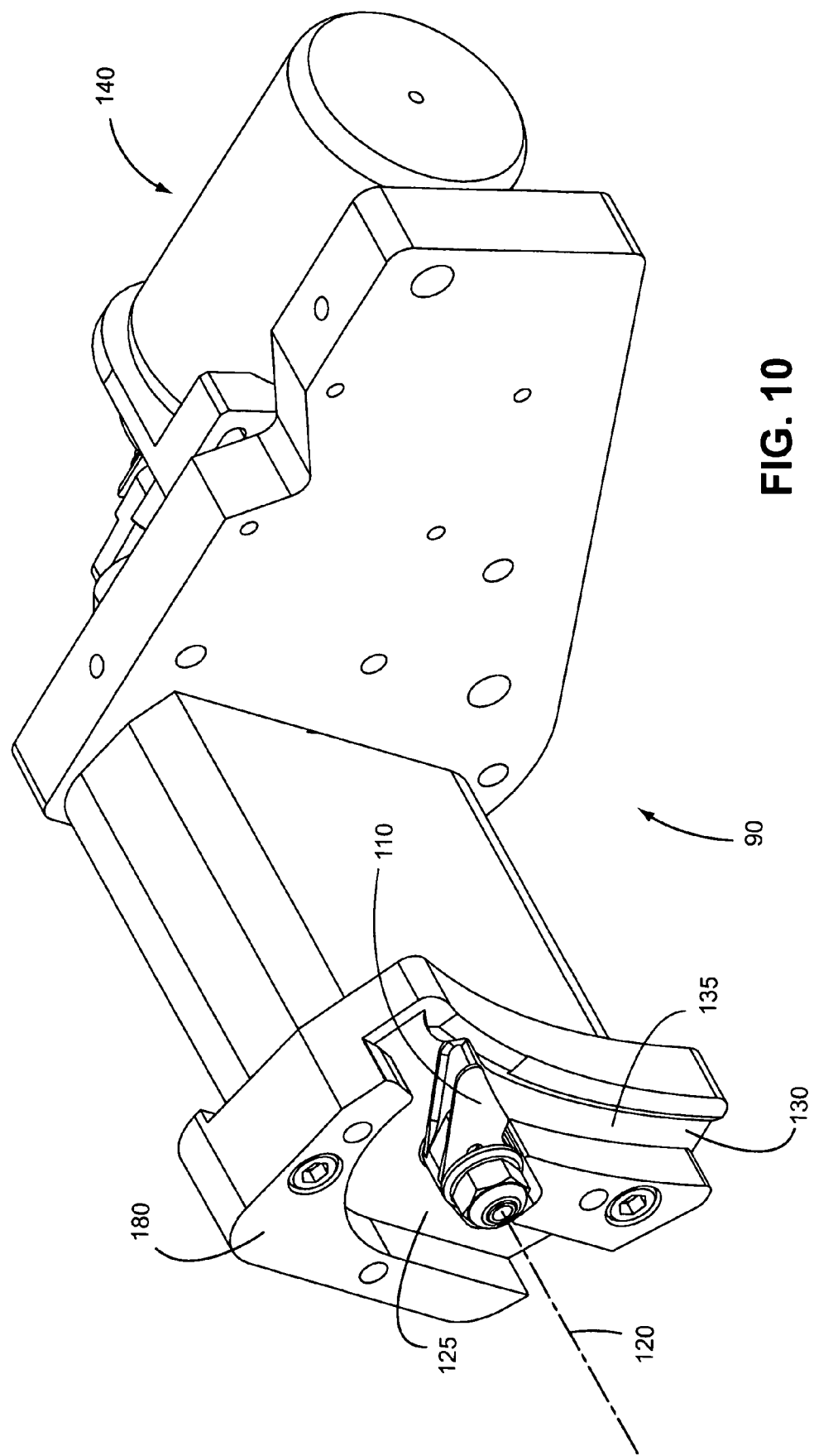
FIG. 10 is a perspective view of the ejection system according to an embodiment of the invention.
Figure 13:
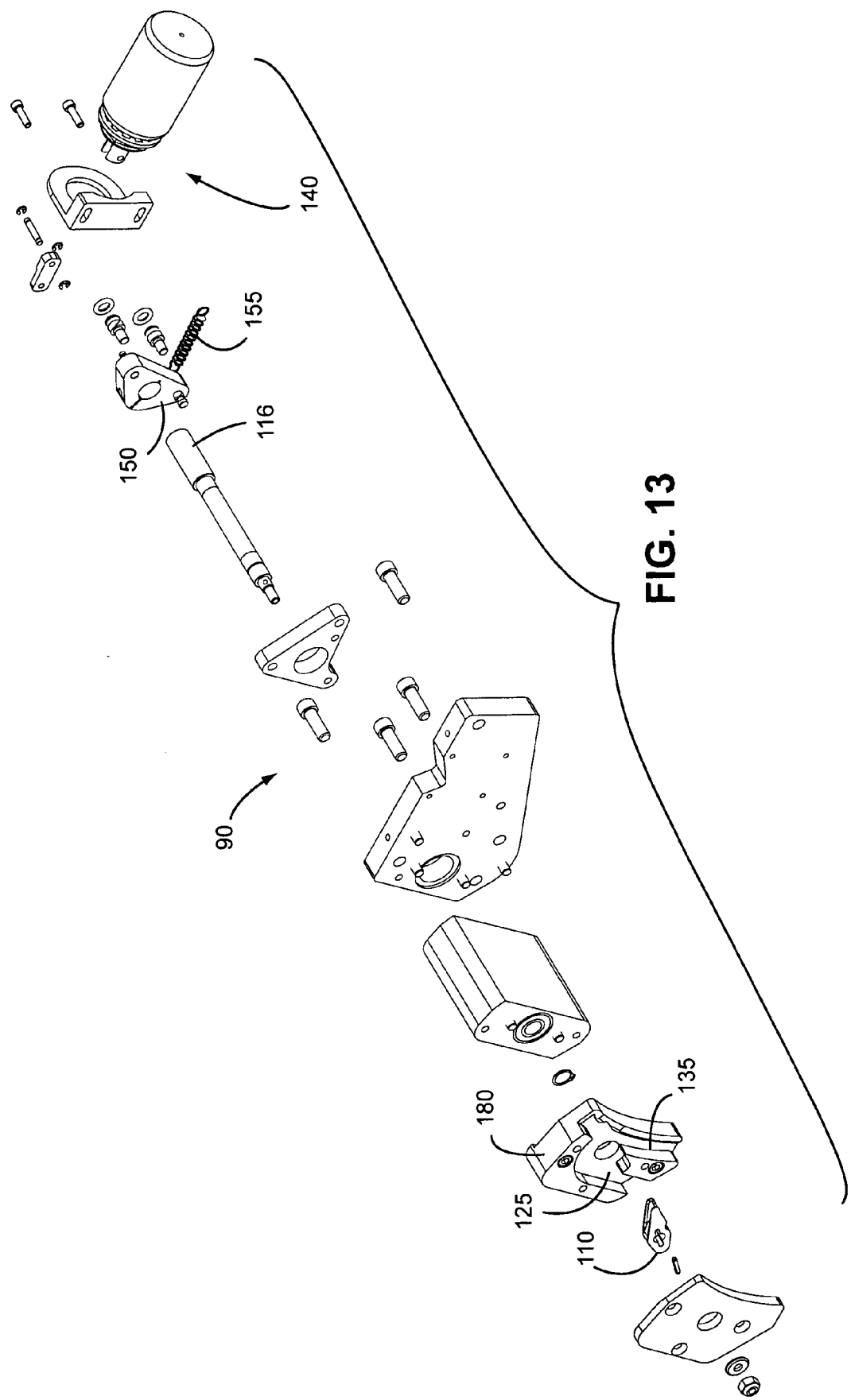
FIG. 13 is an exploded view of the ejection system according to an embodiment of the invention.

FIGS. 10 and 13 show additional housing parts and mounting structures of the ejection system 90, including the housing part 180 providing the channels 125, 135 for guiding the tablets into respective discharge chutes.

FIGS. 14 to 17C illustrate an ejection system 90' according to another embodiment of the invention. The ejection system may be operable with the apparatus 100 and carrier links 105 described above.

The ejection system 90' includes at least one ejection finger 110' positioned adjacent the carrier link as it passes along the conveyer path. Preferably, a pair of ejection fingers 110' are provided, one on each side of the carrier link as shown in the illustrated embodiment. Each ejection finger 110' includes a main body 111' and a tablet engaging member 112' extending from the main body.

Figure 14:
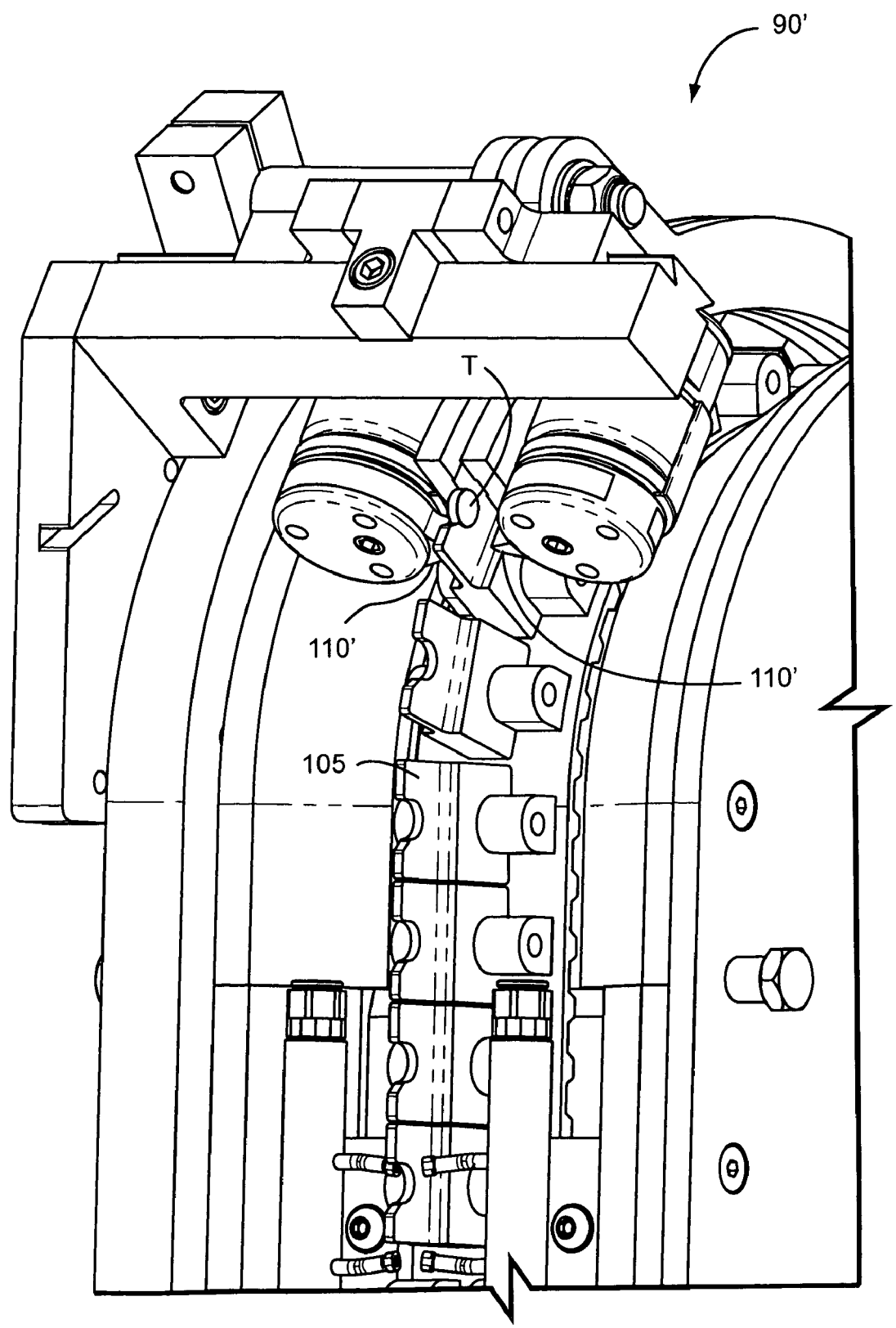
FIG. 14 is a perspective view of a conveyer apparatus including an ejection system according to another embodiment of the invention, the ejection system in non-ejection position.
Figure 17A:
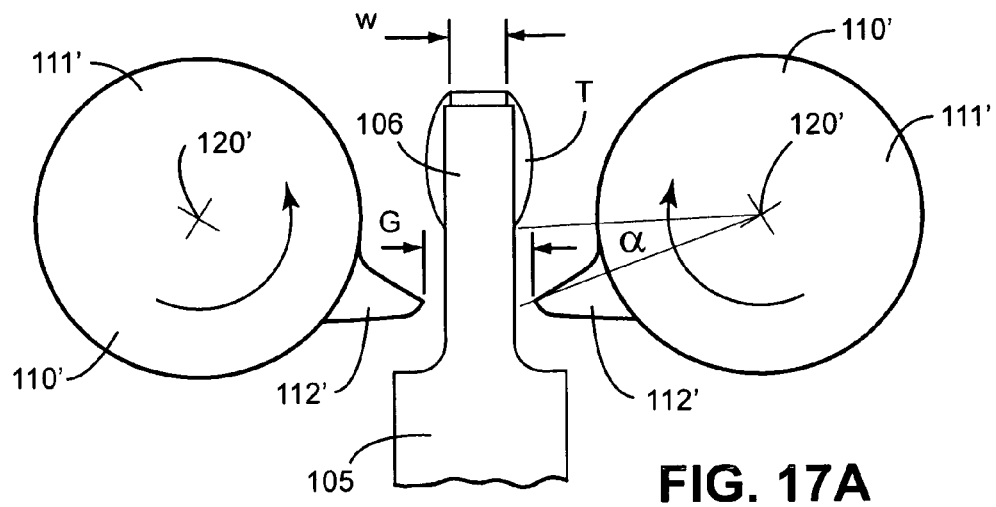
FIGS. 17A, 17B, and 17C are schematic views of the ejection system of FIG. 14 in non-ejection, intermediate, and ejection positions.

The main body or base of each ejection finger 110' is rotatably mounted for rotational movement about an axis 120' to position the tablet engaging member 112' into or out of the path of the tablet. The normal or non-ejection position for the ejection finger is shown in FIGS. 14 and 17A, where the tips of the tablet engaging members are positioned below the tablet, but with enough clearance for the link to pass between the opposed finger tips. This allows the carrier link 105 and tablet T to convey past the ejection system without diverting the tablet.

Specifically, the width of the gap G between the tips of the tablet engaging members 112' in the normal or non-ejection position is larger than the width w of tablet carrier portion 106 of the carrier link 105 (e.g., see FIG. 17A). This allows the carrier link 105 to pass between the gap G, with the tablet T being positioned above (or otherwise offset from) the finger tips.

Figure 15:
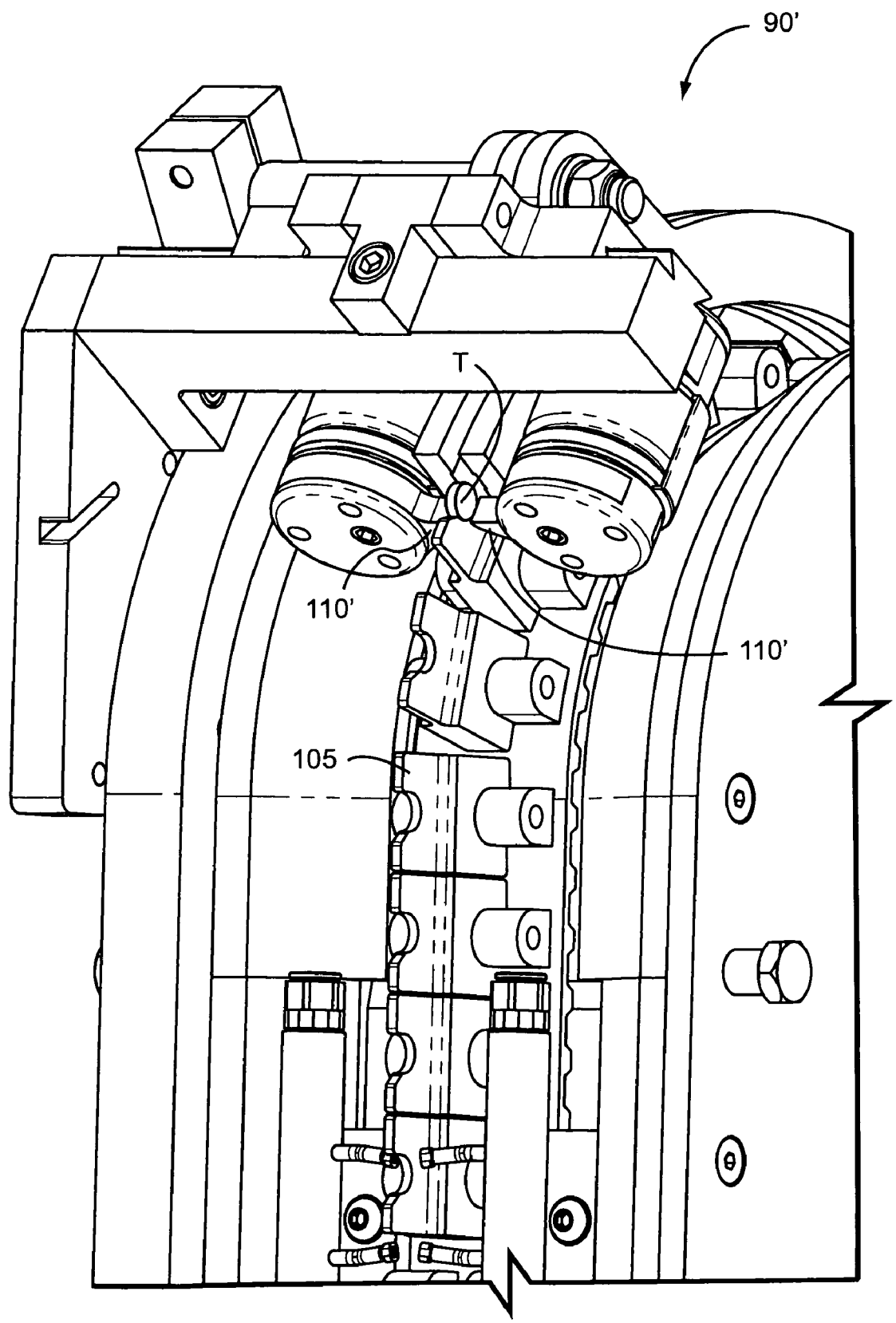
FIG. 15 is a perspective view of the ejection system of FIG. 14 in an intermediate ejection position.
Figure 16:
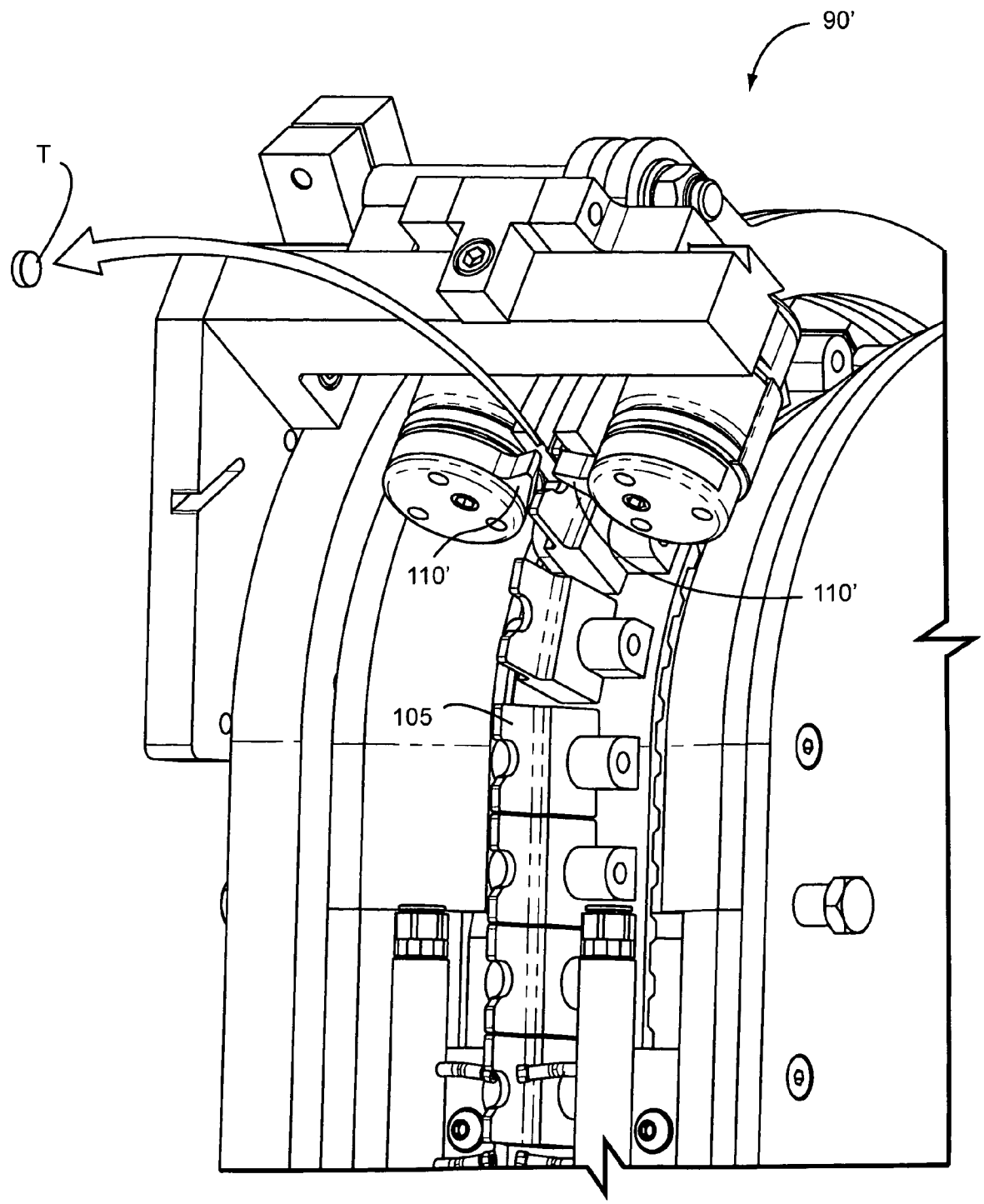
FIG. 16 is a perspective view of the ejection system of FIG. 14 in an ejection position.
Figure 17B:
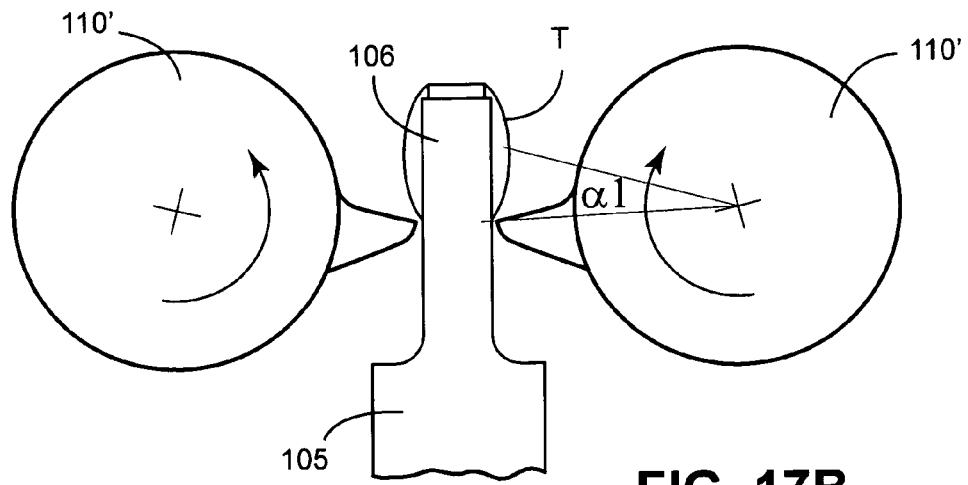
Figure 17C:
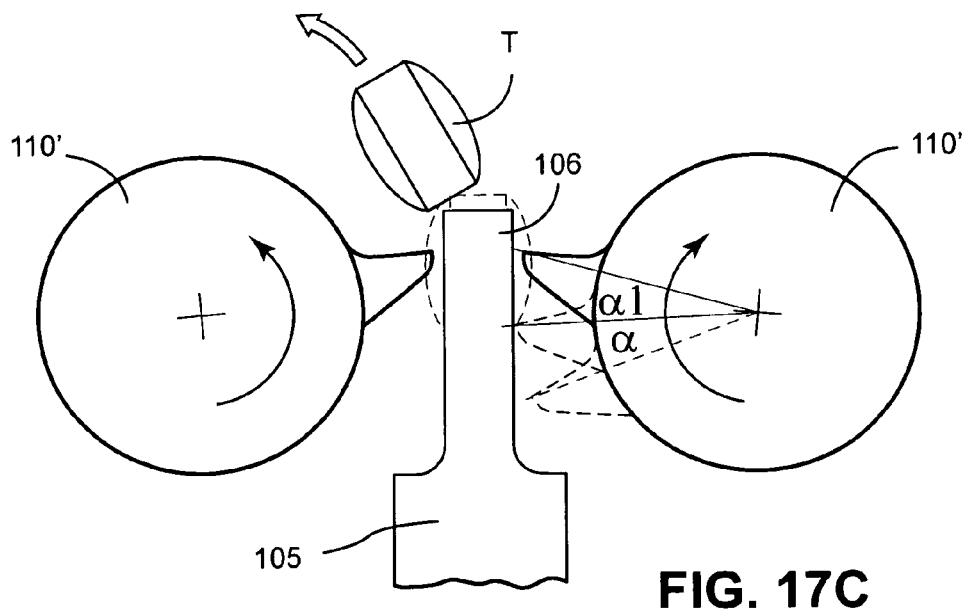

When an appropriate signal is generated indicating that an individual tablet needs to be ejected, the fingers 110' are rotated towards the tablet to eject a tablet indicated by arrows in FIGS. 17A to 17C, such that the tips of the tablet engaging members 112' engage opposite sides of the tablet and discharge the tablet from the pocket of the carrier link 105. FIGS. 15 and 17B show the initial rotation of the fingers, just as they engage the tablet, while FIGS. 16 and 17C show the fingers being further rotated, to eject the tablet T.

FIG. 17C shows the position of the fingers in phantom lines corresponding to those shown in FIGS. 17A and 17B. The fingers rotate in a contra-rotating fashion, i.e., opposite to one another, when ejecting a tablet as best shown in FIGS. 17A to 17C. When returning to the normal or home position shown in FIG. 14 or 17A, the fingers contra-rotate in a direction that is opposite to the arrows shown in FIGS. 17A to 17C.

As shown in FIG. 17A, the tip of each tablet engaging member 112' is positioned at an angle a with respect to the bottom side of the tablet. The magnitude of the angle ranges from about 5-50°, e.g., about 10-30°. This provides a safe distance between the finger tips and the tablet T, to prevent inadvertent contact with the tablet.

When the carrier link 105 travels past the finger 110', the tablet T may be lifted out of the pocket of the carrier link pocket by the ejection finger 110'. Thus, it is possible to selectively eject a single tablet T from its carrier link, without affecting the travel of adjacent (non-defective) tablets T, e.g., without also removing the non-defective tablets preceding or following the defective tablet. In an embodiment, as shown in FIG. 17B, each ejection finger may engage and rotate past the tablet within an angle a1 of about 5-50°, e.g., about 10-30°.

The tablet may be discharged along a channel, to be diverted to a unique discharge chute on the machine.

After the carrier link has traveled past the ejection point provided by the ejection fingers, the ejection fingers are pivoted back into the normal or non-ejection position and out of the path of the carrier links (e.g., see FIGS. 14 and 17A). At no point is the spacing or gap G between the tablet engaging members of the fingers less than the width w of the link 105.

The "acceptable" tablets T are allowed to pass through the ejection system without being diverted by the ejection fingers 110', and are discharged into a separate unique machine discharge chute for "acceptable" tablets.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment.

What is claimed is:

1. A conveyer apparatus for transporting and processing tablets, each of the tablets including a first side, a second side opposite the first side, and a belly band that interconnects the first and second sides, the conveyer apparatus comprising:
    a conveyer including a plurality of carrier links to convey a plurality of tablets along a predetermined conveyer path, each carrier link having a pocket to receive and transport a tablet in a vertical orientation along the predetermined conveyer path; and
    an ejection system structured to selectively accept or eject a tablet from the carrier link in response to a signal provided by a sensor positioned upstream of the ejection system, the ejection system including at least one ejection finger movable between a non-ejection position in which the ejection finger is positioned out of the conveyer path of the carrier link and an ejection position in which the ejection finger is positioned with respect to the carrier link to contact and eject the tablet from the carrier link,
    wherein at least a portion of the ejection finger defines a width that is smaller than a tablet width of the tablet and larger than a link width of the carrier link.

2. A conveyer apparatus according to claim 1, wherein the ejection finger is pivotally movable between the non-ejection and ejection positions.

3. A conveyer apparatus according to claim 1, wherein the sensor includes an inspection unit structured to detect defective or flawed tablets.

4. A conveyer apparatus according to claim 1, wherein the ejection system is controlled to eject defective or flawed tablets.

5. A conveyer apparatus according to claim 1, wherein the ejection system is controlled to eject non-defective or acceptable tablets.

6. A conveyer apparatus according to claim 1, wherein the signal actuates a solenoid that effects pivotal movement of the ejection finger.

7. A conveyer apparatus according to claim 1, further comprising one or more processing stations provided along the conveyer path upstream of the ejection system.

8. A conveyer apparatus according to claim 7, wherein the processing station includes a marking apparatus.

9. A conveyer apparatus according to claim 1, wherein the ejection finger includes a main body and spaced-apart tablet engaging members extending from the main body, the tablet engaging members defining a slotted opening that defines the width of the ejection finger.

10. A conveyer apparatus according to claim 1, wherein the ejection system includes a housing defining a channel to guide ejected tablets from the ejection finger to a discharge chute.

11. A conveyer apparatus according to claim 1, wherein the ejection system is positioned along the conveyer path wherein the conveyer path transitions from a generally horizontal portion to a generally vertical portion.

12. A conveyer apparatus according to claim 11, wherein the upper surface is oriented about 15-25° downwardly from horizontal.

13. A conveyer apparatus according to claim 1, wherein the ejection finger in the ejection position defines an upper surface to guide ejected tablets, the upper surface being oriented such that it is ramped downwardly from horizontal.

14. A conveyer apparatus according to claim 1, wherein the ejection finger is a first ejection finger and the ejection system further comprises a second ejection finger, the first and second ejection fingers positioned on respective sides of the carrier link.

15. A conveyer apparatus according to claim 14, wherein each ejection finger includes a tablet engaging member, and the tablet engaging members of the first and second ejection fingers define the width therebetween.

16. A conveyer apparatus for transporting and processing tablets, each of the tablets including a first side, a second side opposite the first side, and a belly band that interconnects the first and second sides, the conveyer apparatus comprising:
    a conveyer including a plurality of carrier links to convey a plurality of tablets along a predetermined conveyer path, each carrier link having a pocket to receive and transport a tablet in a vertical orientation along the predetermined conveyer path; and
    an ejection system structured to selectively accept or eject a tablet from the carrier link in response to a signal provided by a sensor positioned upstream of the ejection system, the ejection system including a pair of ejection fingers positioned on respective sides of the carrier links, the ejection fingers movable between a non-ejection position in which the ejection fingers are positioned out of the conveyer path of the carrier link and an ejection position in which the ejection fingers are positioned with respect to the carrier link to contact and eject the tablet from the carrier link, wherein the ejection fingers define a width therebetween that is smaller than a tablet width of the tablet and larger than a link width of the carrier link.

17. A conveyer apparatus according to claim 16, wherein the ejection fingers are rotatable between the non-ejection and ejection positions.

18. A conveyer apparatus according to claim 17, wherein the ejection fingers contra-rotate with respect to one another.

19. A conveyer apparatus according to claim 16, wherein the sensor includes an inspection unit structured to detect defective or flawed tablets.

20. A conveyer apparatus according to claim 16, wherein the ejection system is controlled to eject defective or flawed tablets.

21. A conveyer apparatus according to claim 16, wherein the ejection system is controlled to eject non-defective or acceptable tablets.

22. A conveyer apparatus for transporting and processing tablets, each of the tablets including a first side, a second side opposite the first side, and a belly band that interconnects the first and second sides, the conveyer apparatus comprising:

a single row conveyer including a plurality of carrier links to convey a plurality of tablets along a predetermined conveyer path, each carrier link having a pocket to receive and transport an individual tablet in a vertical orientation along the predetermined conveyer path; and an ejection system structured to selectively accept or eject a tablet from the carrier link in response to a signal provided by a sensor positioned upstream of the ejection system, the sensor configured to generate the signal based on one or more predetermined criteria, and the ejection system includes a first ejection finger and a second ejection finger positioned on respective sides of the carrier link to eject only the selected tablet from the carrier link without affecting tablets in adjacent carrier links not associated with the predetermined criteria.

23. A conveyer apparatus according to claim 22, wherein the ejection system includes a controller to compare the signal against the predetermined criteria.

24. A conveyer apparatus according to claim 22, wherein the sensor includes an inspection unit structured to detect defective or flawed tablets.

25. A conveyer apparatus according to claim 22, wherein the ejection system is controlled to eject defective or flawed tablets.

26. A conveyer apparatus according to claim 22, wherein the ejection system is controlled to eject non-defective or acceptable tablets.

27. A conveyer apparatus according to claim 22, wherein the at least ejection finger is movable between a non-ejection position in which the ejection finger is positioned out of the conveyer path of the carrier link and an ejection position in which the ejection finger is positioned with respect to the carrier link to contact and eject the tablet from the carrier link.

28. A conveyer apparatus according to claim 22, wherein the signal actuates a solenoid that effects pivotal movement of the ejection finger.

29. A conveyer apparatus according to claim 22, further comprising one or more processing stations provided along the conveyer path upstream of the ejection system.

30. A conveyer apparatus according to claim 29, wherein the processing station includes a marking apparatus.

31. A conveyer apparatus according to claim 22, wherein at least a portion of the ejection finger defines a width that is smaller than a tablet width of the tablet and larger than a link width of the carrier link.

* * * * *